(12) United States Patent
Yamashita et al.

(10) Patent No.: US 7,439,334 B2
(45) Date of Patent: Oct. 21, 2008

(54) METHOD OF ARRANGEMENT OF TITANIUM-BINDING FERRITIN AND INORGANIC PARTICLES

(75) Inventors: Ichiro Yamashita, Nara (JP); Kiyotaka Shiba, Tokyo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 30 days.

(21) Appl. No.: 11/354,864

(22) Filed: Feb. 16, 2006

(65) Prior Publication Data

US 2006/0257931 A1 Nov. 16, 2006

Related U.S. Application Data

(63) Continuation of application No. PCT/JP2005/021510, filed on Nov. 24, 2005.

(30) Foreign Application Priority Data

Dec. 14, 2004 (JP) ............................. 2004-361987
Jan. 13, 2005 (JP) ............................. 2005-006720

(51) Int. Cl.
*C07K 14/00* (2006.01)
*H01L 21/00* (2006.01)
*H01L 21/314* (2006.01)
*H01L 21/471* (2006.01)

(52) U.S. Cl. ..................... 530/400; 438/778; 435/7.1
(58) Field of Classification Search ............ 435/7.1
See application file for complete search history.

(56) References Cited

U.S. PATENT DOCUMENTS

2003/0124741 A1 7/2003 Yamashita

FOREIGN PATENT DOCUMENTS

JP 11-204774 7/1999

JP 2003-033191 2/2003

OTHER PUBLICATIONS

A.S. Blawas et al., Protein Patterning,vol. 19, Issues 7-9, Apr. 5, 1998, NSF/ERC Center For Emerging Cardiovascular Technologies, Department of Biomedical Engineering, Duke University Durham, NC 27708 USA.
Ki-Bum Lee et. al., Protein Nanoarrays Generated By Dip-Pen Nanolithography, vol. 295, Northwestern University, Department of Chemistry and Center for Nanofabrication and Molecular Self-Assembly, IL, USA.
A. Bernard et al., Microcontact Printing of Proteins, Advanced Materials, vol. 12, p. 1067-1070, Jul. 13, 2000, Winheim, Fed. Rep. of Germany 3PC -172 ,Nov. 25, 2003 p. 62-63, Feb. 26, 1990.
Ken-Ichi Sano et al. A Hexapeptide Motif that Electrostatically Binds to the Surface of Titanium. Department of Protein Engineering, Caner Institute, Japanese Foundation for Cancer Research, and CREST, JST, Tokyo Japan 1030 3PB-613 Nov. 25, 2004.
Method of Selective Arrangement of Ferritin, Matsushita Electric Industrial Co., Ltd., U.S. Appl. No. 11/385,006, filed Mar. 21, 2006.
Ken'ichi Sano et al., "Titanium Hyomen ni Seidenteki ni Ketsugo suru Hexapeptide Motif no Tanri (Hexapeptide Motif that Electrostatically Binds to the Surface of Titanium)," 26th Annual Meeting of the Molecular Biology Society of Japan, Nov. 25, 2003, p. 917, 3PC-172.
"Tanpakushitsu I -Bunri Seisei Seishitsu," Tokyo Kagaku Dojin, Feb. 26, 1990, pp. 62-63, ed. The Japanese Chemical Society.
Ken'ichi Sano et al., "Titanium Zairyo Hyomen ni Kyuchaku shi Kotsusaibo Secchaku ni Eikyo o Ataeru Jinko Peptide (Attachment of osteoblastic cells to titanium surface b y an artificial peptide),", 27th Annual Meeting of the Molecular Biology Society of Japan, Nov. 25, 2004, pp. 1030, 3PB-613.

*Primary Examiner*—Maraym Monshipouri
*Assistant Examiner*—Marsha M Tsay
(74) *Attorney, Agent, or Firm*—McDermott Will & Emery LLP

(57) ABSTRACT

A method for selectively arranging ferritin modified with a peptide, which specifically binds to titanium, to titanium formed on a substrate surface is provided.

The method for arranging ferritin of the present invention is characterized in that ferritin is selectively bound on titanium on a substrate by modifying the N-terminal part of ferritin with a peptide which specifically binds to titanium. Also, the method for arranging ferritin of the present invention is characterized in that selectivity for titanium can be markedly improved by adding a nonionic surface activating agent.

15 Claims, 14 Drawing Sheets

METHOD OF ARRANGEMENT OF TITANIUM-BINDING FERRITIN AND INORGANIC PARTICLES

This is a continuation application under U.S.C 111(a) of pending prior International application No. PCT/JP2005/021510, filed on Nov. 24, 2005, which in turn claims the benefit of Japanese Application No. 2004-361987 filed on Dec. 14, 2004, and Japanese Application No. 2005-006720 filed on Jan. 13, 2005, the disclosures of which Applications are incorporated by reference herein.

BACKGROUND OF THE INVENTION

1. Field of the Invention

The present invention relates to a method for allowing titanium-binding ferritin, the surface of which being modified with a peptide that recognizes and binds to titanium, to be selectively aligned on titanium on a substrate surface. Furthermore, the present invention relates to a method for regularly arranging inorganic particles which had been included in titanium-binding ferritin on titanium formed on a substrate.

2. Related Art

Particles (inorganic particles) which include a protein and an inorganic substance and which are arranged on a substrate have attracted attention in industrial fields of catalysts, sensors, biochips, transistors, semiconductors lasers, magnetic discs, displays and the like. In particular, patterning techniques have been desired in which inorganic particles are selectively arranged in a specified region, or they are regularly arranged in a fine region of nano-size, when the inorganic particles are industrially applied. Furthermore, in recent years, aiming at miaturization of total analysis systems including biosensors, applications to fine chemical substance analysis systems (Micro Total Analysis System (μTAS)) have also attracted attention. Behind such a situation, advantages such as improvement of biocompatibility, enablement of lowering of the cost due to mass productivity and measurement in the place (being portable) and the like are involved.

Techniques for selectively arranging proteins or inorganic particles on a solid surface involve extraordinary difficulty because it is very difficult to allow the surface of the protein and the inorganic substance to have a self-recognizing function. Known methods for forming a fine pattern using a protein that is a biomolecule include a method in which photolithography is utilized (see, A. S. Blawas, W. M. Reichert, *Biomaterials,* 19, 595 (1998)), microcontact printing (see, A. Bernard, J. P. Renault, B. Michel, H. R. Bosshard, E. Delamarche, *Adv. Mater.,* 12, 1067 (2000)), dip-pen nanolithography (see, K. B. Lee, S. J. Park, C. A. Mirkin, J. C. Smith, M. Mrksick, *Science,* 295, 1702 (2002)), and the like. However, in light of mass productivity and costs, techniques for carrying out patterning of fine particles in a nano-size region have been demanded. Furthermore, a method for regularly arranging nano-size particles surrounded by a protein molecule is disclosed in Japanese Patent Provisional Publication No. H11-204774.

In these methods, procedures of: subjecting the surface of a SAM membrane (self-assembled monomolecular membrane), an LB membrane (monomolecule accumulating membrane) or the like to a processing for selectively arranging the particles; executing patterning of the particles through further conducting photolithography in combination; forming a region in which the inorganic particles are selectively arranged on a substrate by direct drawing or the like of a pattern on the substrate with a nanoprobe such as AFM (Atomic Force Microscope) or the like; and thereafter arranging the inorganic particles.

Hereinafter, a method for arranging inorganic particles using an LB membrane (PBLH membrane) according to the conventional method (Japanese Patent Provisional Publication No. H11-204774) will be illustrated with reference to FIGS. 1A to 1H.

First, in the step shown in FIG. 1A, a buffer 11 is reserved in a water bath 10 made of Teflon™, and naturally occurring ferritin 21 including an inorganic particle 20 therein is dispersed in this buffer.

Next, in the step shown in FIG. 1B, a PBLH membrane 30 is overlaid on the liquid surface of the solution. Then, the pH is adjusted with an appropriate acid alkaline solution. Because ferritin is negatively charged contrary to the PBLH membrane surface being positively charged, the naturally occurring ferritin 21 is attached on the PBLH membrane.

Next, in the step shown in FIG. 1C, a substrate (silicon substrate) 40 which had been subjected to a hydrophobic surface treatment is floated on the liquid surface on which the PBLH membrane was overlaid, thereby allowing the PBLH membrane on which the naturally occurring ferritin is attached to be adhered on the substrate.

Next, in the step shown in FIG. 1D, the silicon substrate 40 having the adhered PBLH membrane on which the naturally occurring ferritin is attached is removed from the water bath.

Next, in the step shown in FIG. 1E, after covering the surface of the face on which the naturally occurring ferritin is attached with a buffer solution 11, ultraviolet irradiation is performed using an adequate mask pattern 50. The naturally occurring ferritin in the region on which ultraviolet ray was irradiated is decomposed, and dispersed in the solution.

Next, in the step shown in FIG. 1F, the silicon substrate 40 after executing the patterning shown in FIG. 1E is washed with water.

Next, in the step shown in FIG. 1G, the silicon substrate 40 is dried to obtain the pattern arrangement of the naturally occurring ferritin including the inorganic particle therein.

Thereafter, in the step shown in FIG. 1H, a heat treatment at 500° C. is carried out in an inert gas 60 (for example, in nitrogen) to bake to burn out the naturally occurring ferritin including the inorganic particle therein and the PBLH membrane, thereby providing secondary pattern arrangement of the inorganic particles on the substrate. This structure is further processed to give a structure required for the device as described above.

However, according to the aforementioned conventional method, the SAM membrane is formed on the substrate side, and patterning is executed on the SAM membrane using an ultraviolet ray, or an LB membrane that is an adsorption membrane of the inorganic particle is utilized as the intermediate layer with respect to the substrate. Therefore, there are possibilities that the steps may be complicated, or that impurities included in the constituents of the SAM membrane or the LB membrane, or in the solution remain on the arranged surface of the inorganic particles whereby causing adverse influences on the device. Accordingly, an object of the present invention is to provide a technique for selectively and regularly arranging inorganic particles, in particular, those having a diameter of several to several ten nanometers in a necessary region and in a necessary amount with high mass productivity at low costs, without need of an intermediate layer, by allowing the inorganic particle side to have a recognizing ability of the base material on a substrate.

SUMMARY OF THE INVENTION

In order to accomplish the object described above, an aspect of the present invention is characterized in that binding force between ferritin and titanium on the substrate surface is controlled by modifying the N-terminal part of ferritin with a peptide which recognizes and binds to titanium. This action of the peptide enables the binding force between ferritin and the substrate to be controlled, thereby allowing the ferritin to be adsorbed and arranged selectively in the titanium part. In other words, it becomes possible to allow the ferritin itself to have an ability of augmenting inherent binding force between titanium on the substrate or other part and the ferritin, or of lowering such force to the contrary (self-recognizing ability).

The term "modification of N-terminal part of ferritin with a peptide" referred to herein involves any of: substitution of N-terminal amino acid residue (methionine residue) of ferritin with a titanium-binding peptide, addition of a titanium-binding peptide at the N-terminus of ferritin, and insertion of a titanium-binding peptide at the amino acid sequence of the N-terminal part of ferritin.

Also, when an inorganic particle is included in the titanium-binding ferritin, arrangement of the inorganic particle included in the titanium-binding ferritin on titanium on the substrate is also enabled.

In contrast, when any inorganic particle is not included in the titanium-binding ferritin, arrangement of the inorganic particle cannot be executed on titanium on the substrate, but protection of titanium by the titanium-binding ferritin is enabled.

As a process for determining the amino acid sequence which specifically binds/adsorbs to a certain substance, a biopanning process by a phage peptide library may be exemplified. In this process, a phage (a virus that infects *Escherichia coli*) population in which random peptide sequences are displayed is used to screen a peptide that selectively binds to a particular substance among them.

This process is a technique which can elucidate a specific interaction to a particular substance with respect to biomolecules, and can synthesize an artificial protein having a design of a multifunctional micro gene or having a complex function of a novel combination that has not been present in naturally occurring proteins. In recent years, this technique has enabled synthesis of an artificial peptide that specifically binds to an inorganic substance such as a metal or the like.

The present invention relates to a method for arranging titanium-binding ferritin, which ferritin being modified with a peptide on the surface thereof, the peptide having an amino acid sequence that specifically binds to titanium, and being isolated using this biopanning method.

Moreover, the present invention is characterized in that binding force between the titanium-binding ferritin and titanium on the substrate is further selectively controlled by a nonionic surface activating agent. Although the nonionic surface activating agent fundamentally has a function to attenuate the binding force between the protein and the substrate that is an inorganic substance through acting on the interface between them. Thus, this action enables attenuation of only the binding force between the titanium-binding ferritin and the inorganic material other than titanium on the substrate. In other words, according to this process, elevation of base material selectivity of titanium-binding ferritin (ratio of proteins adsorbed in regions where arrangement of particles is required and not required), and effective control of the amount of adsorption of the titanium-binding ferritin that adsorbs in the region where arrangement is required.

Specifically, the present invention relates to a method for selectively arranging ferritin, the method comprising a binding step in which a solution containing a titanium-binding ferritin including modification at the subunit N-terminal part with a peptide set out in SEQ ID NO: 1 which recognizes and binds to titanium is added dropwise onto a substrate with titanium formed on the part of the surface thereof, thereby allowing the titanium-binding ferritin to be selectively bound to titanium.

Modification of the subunit N-terminal part of ferritin with a peptide that recognizes and specifically binds to titanium (SEQ ID NO: 1) enables specific binding of ferritin with titanium on the substrate. Thus, ferritin can be selectively arranged on titanium on the substrate.

When the solution further contains a nonionic surface activating agent, and when the method comprises following the binding step a removing step in which the nonionic surface activating agent is removed from on the substrate, selectivity of the titanium-binding ferritin can be further elevated. After selectively arranging the titanium-binding ferritin on titanium on the substrate, the nonionic surface activating agent can be removed by washing the substrate.

Similar effect can be also achieved when the method comprises prior to the binding step a covering step in which the substrate is covered with a nonionic surface activating agent.

In any of these cases, it is preferred that the concentration of the nonionic surface activating agent is 0.006 v/v % or greater and 10 v/v % or less.

Because ferritin has a void space inside, the titanium-binding ferritin can also include an inorganic particle (for example, $Fe_2O_3$) therein.

Following the binding step, a solution containing ferritin other than the titanium-binding ferritin is added dropwise to the substrate, thereby also capable of arranging ferritin other than the titanium-binding ferritin, in a part other than titanium on the substrate.

Heating of the substrate with the titanium-binding ferritin arranged thereon results in decomposition of the titanium-binding ferritin, thereby also capable of selectively fixing and arranging the inorganic particle which had been included in the titanium-binding ferritin on titanium on the substrate.

In other words, the present invention relates to a method for arranging inorganic particles, the method comprising a binding step in which a solution containing a titanium-binding ferritin including the inorganic particle therein and including modification at the subunit N-terminal part with a peptide set out in SEQ ID NO: 1 which recognizes and binds to titanium is added dropwise onto a substrate with titanium formed on the part of the surface thereof, thereby allowing the titanium-binding ferritin to be selectively bound to titanium on the substrate, and a decomposition step in which the substrate is heated to decompose the titanium-binding ferritin.

Furthermore, the present invention relates to a method for arranging inorganic particles, the method comprising a binding step in which a solution containing a titanium-binding ferritin including modification at the subunit N-terminal part with a peptide set out in SEQ ID NO: 1 which recognizes and binds to titanium is added dropwise onto a substrate with titanium formed on the part of the surface thereof, thereby allowing the titanium-binding ferritin to be selectively bound to titanium on the substrate, an arranging step in which a solution containing ferritin other than the titanium-binding ferritin and including an inorganic particle therein is added dropwise onto the substrate, thereby arranging ferritin including the inorganic particle therein, in a part other than titanium on the substrate, and a decomposition step in which the substrate is heated to decompose ferritin on the substrate.

By selectively arranging titanium-binding ferritin on titanium on a substrate using the method for arranging titanium-binding ferritin as described above, production of a biodevice which utilizes a property inherent to titanium-binding ferritin is enabled.

Exemplary biodevice may be biosensors or biochips.

According to the method for arranging titanium-binding ferritin of the present invention, when titanium-binding ferritin and the inorganic particle included therein are arranged and fixed on a substrate, the physical adsorbing force between the ferritin and the titanium formed on the substrate can be controlled by modifying the ferritin surface (N-terminal part) with a peptide that recognizes titanium (SEQ ID NO: 1), and secondary regular arrangement of the ferritin on the substrate is also enabled. According to the method for arranging titanium-binding ferritin of the present invention, the inorganic particles can be arranged in the region where required in a necessary amount, or the inorganic particles can be arranged on the substrate with high accuracy in a regular manner, with high mass productivity and favorable cost performances.

DETAILED DESCRIPTION OF THE INVENTION

The foregoing objects, other objects, features and advantages of the present invention will be apparent from the following detailed description of preferred embodiments with reference to attached drawings.

Modes for carrying out the present invention will be explained below with appropriate references to the drawings. However, the present invention is not limited thereto.

(Principles of the Present Invention)

Principles of the present invention will be explained first. In this section, a method for arranging titanium-binding ferritin and a method for arranging inorganic particles on a substrate will be explained.

[Method for Arranging Titanium-Binding Ferritin]

Figure 1A:
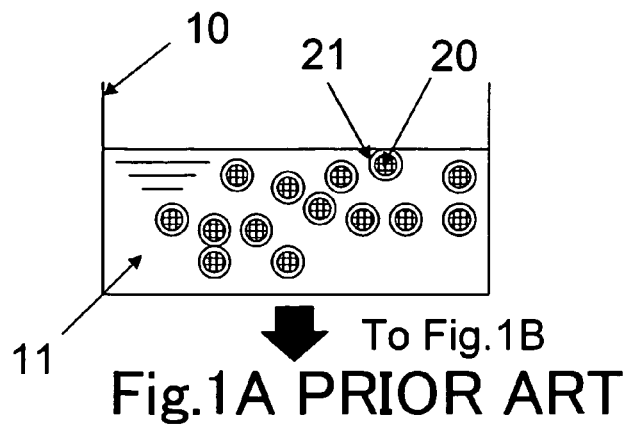
FIGS. 1A to 1H show an explanatory view illustrating the steps of a conventional method for arranging inorganic particles.
Figure 1B:
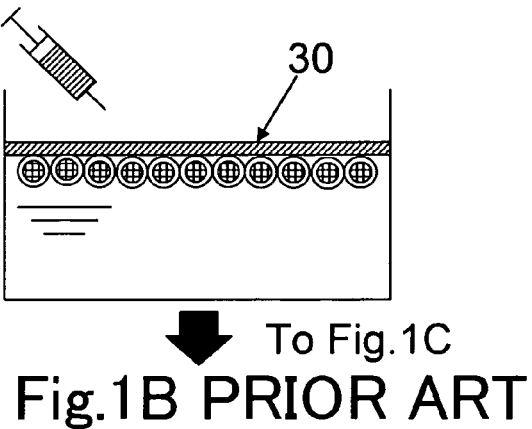
Figure 1C:
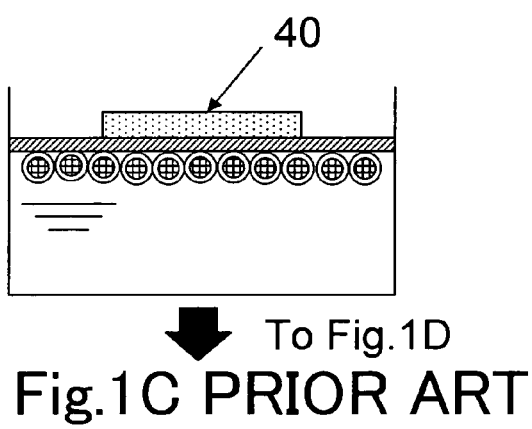
Figure 1D:
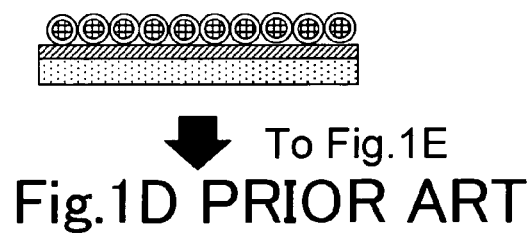
Figure 1E:
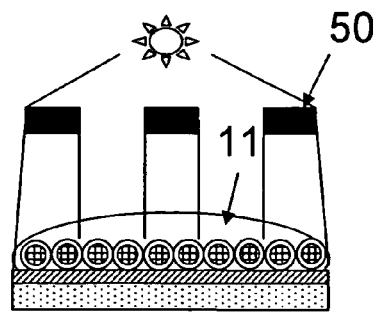
Figure 1F:
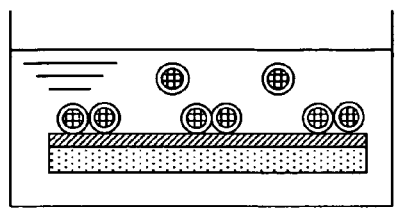
Figure 1G:
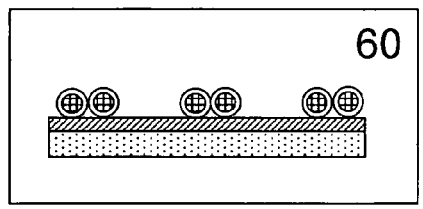
Figure 1H:
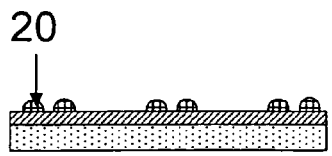
Figure 2:
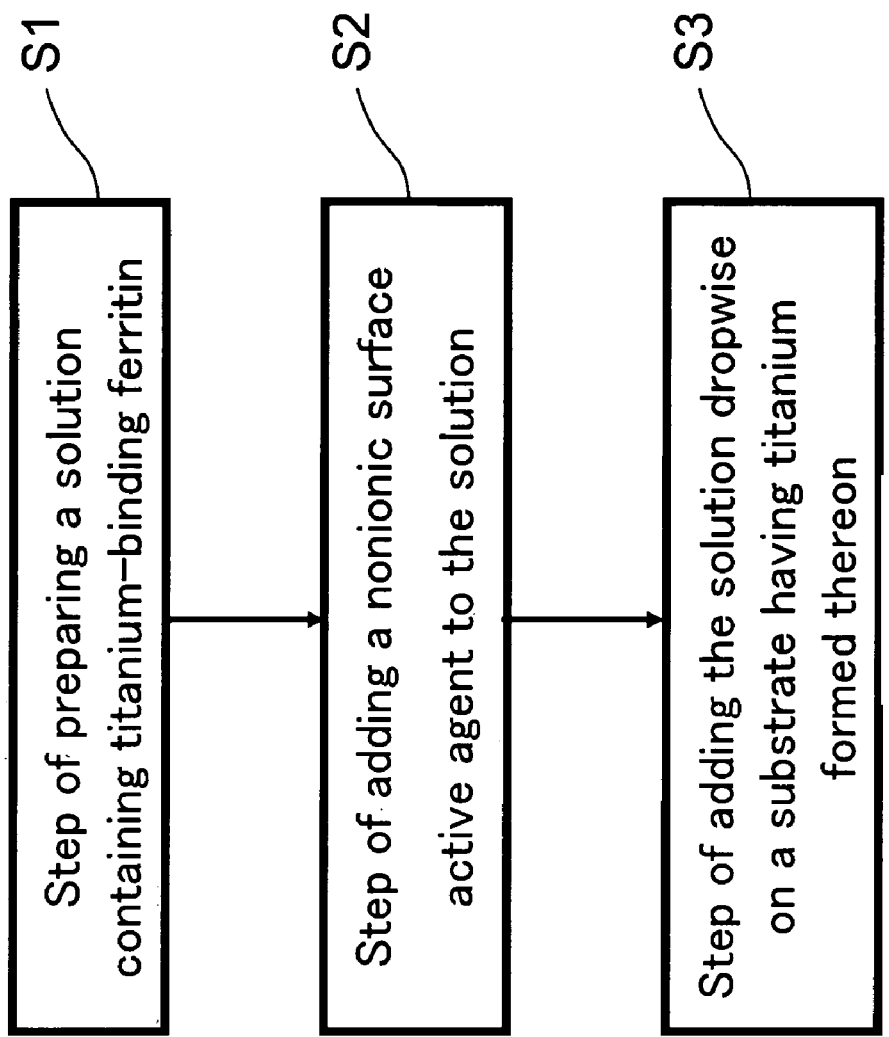
FIG. 2 shows a flowchart conceptually illustrating the method for arranging titanium-binding ferritin of the present invention.

FIG. 2 shows a flow chart conceptually illustrating the method for arranging titanium-binding ferritin of the present invention.

As shown in FIG. 2, the method for arranging titanium-binding ferritin of the present invention includes three steps, i.e., steps S1 to S3.

First, in the step S1, a solution containing titanium-binding ferritin is provided (prepared).

Next, in the step S2, the solution prepared in the step S1 is added dropwise onto the substrate having titanium formed thereon. Accordingly, the titanium-binding ferritin itself recognizes and specifically binds to titanium formed on the substrate.

A step S3 in which a nonionic surface activating agent is added to the solution prepared in the step S1 may be carried out between the step S1 and the step S2. In the method for arranging titanium-binding ferritin of the present invention, selective binding property of the titanium-binding ferritin to titanium can be improved by addition of the nonionic surface activating agent.

Also, the step S1 and the step S2 are explained herein as each independent step, however, the step S1 and the step S2 can be also carried out at the same time as single step.

Moreover, in the embodiment of the present invention, naturally occurring ferritin (derived from equine spleen) was used in place of the titanium-binding ferritin used in the step S1 in Comparative Example. Hereinafter, the method for manufacturing these fine particles will be explained.

<Isolation of Titanium-Binding Polypeptide>

A method for isolating a peptide which specifically binds to titanium by the aforementioned biopanning technique will be explained with reference to FIGS. 3A to 3G. According to this method, a fibrous phage which infects *Escherichia coli* is utilized. The phage has a structure directly covered by several kinds of coat proteins. An exogenous gene is inserted into any one of these coat protein genes, and its product can be displayed at a specified site of the phage particle 70 as a coat protein. By inserting a random synthetic DNA, a polypeptide library having the entire peptide sequence 71 at the N-terminus can be produced.

Figure 3A:
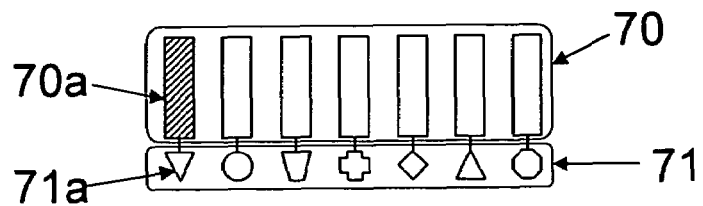
FIGS. 3A to 3G show an explanatory view illustrating a biopanning technique.

Specifically, in the step shown in FIG. 3A, phage particles 70 are provided. In this process, left hand phage particle 70a has a peptide sequence 71a having affinity to the target.

Figure 3B:
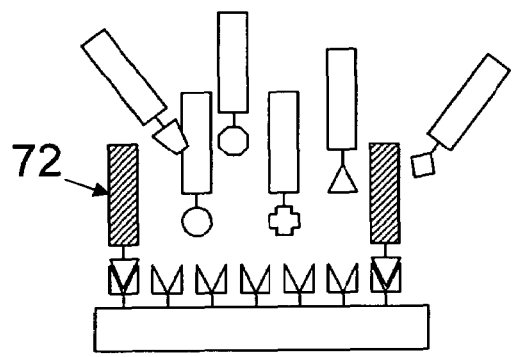

Next, in the step shown in FIG. 3B, screening is carried out based on the affinity (binding property) to a certain target (titanium in the present invention) using the phage peptide library. Specifically, incubation for an adequate time period after adding the phage peptide library solution to the target results in binding of the phage 72 having high affinity to the target.

Figure 3C:
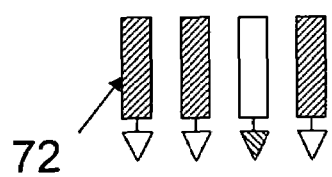

Next, in the step shown in FIG. 3C, the phages which had not bound to the target are washed to remove them, and the phage 72 strongly bound to the target are recovered. This series of processes concentrates the phages 72 having high affinity to the target. Thereafter, the strongly bound phages are recovered from the target by an acid treatment or the like.

Figure 3D:
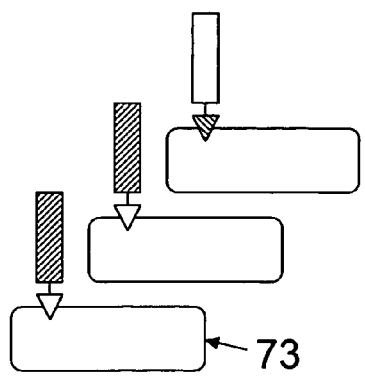

Next, in the step shown in FIG. 3D, the recovered phages that are specific are infected host *Escherichia coli* 73 to allow for amplification.

Figure 3E:
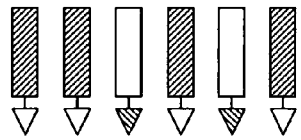

Next, in the step shown in FIG. 3E, the phage clone is recovered from the host *Escherichia coli* 73.

Next, the steps shown in FIGS. 3B to 3E are repeated predetermined times. Accordingly, the phage clone having high affinity to the target is proliferated.

Figure 3F:
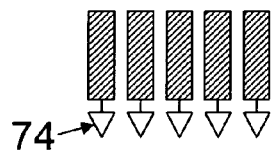

Next, in the step shown in FIG. 3F, the phage clone having high affinity to the target is isolated, and the amino acid sequence 74 which specifically binds to the target is read from the DNA sequence.

Figure 3G:
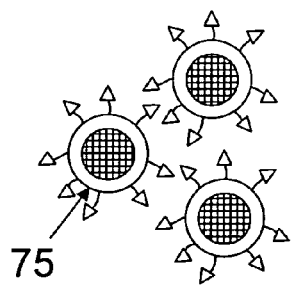

Thereafter, in the step shown in FIG. 3G, a recombinant protein 75 including thus read amino acid sequence added at the N-terminus is synthesized.

Meanwhile, an artificial peptide (SEQ ID NO: 1) that specifically binds to titanium was isolated using this biopanning technique, and it was also elucidated that this artificial peptide electrostatically binds to the titanium surface (see, K. Sano, K. Shiba, J. AM. CHEM. SOC. Vol. 125, No. 47 (2003)). The present invention is characterized in that arrangement of titanium-binding ferritin and inorganic particles included in the titanium-binding ferritin to a specified position (on titanium) on a substrate is carried out using recombinant ferritin including an artificial peptide set out in SEQ ID NO: 1 (peptide that specifically binds to titanium) added at the N-terminal part.

In the embodiments described below, titanium-binding ferritin (TBF, SEQ ID NO: 5) including modification with an artificial peptide (SEQ ID NO: 1) which specifically binds to titanium at the N-terminus was used as the titanium-binding ferritin.

<Method for Manufacturing Recombinant Ferritin>

In the embodiments described below, recombinant ferritin including modification with a titanium-binding polypeptide at the N-terminal part, and recombinant ferritin not having the titanium-binding polypeptide were used as the protein fine particle. In the following, a method for manufacturing recombinant ferritin (RF) not having a titanium-binding polypeptide will be explained.

Figure 4:
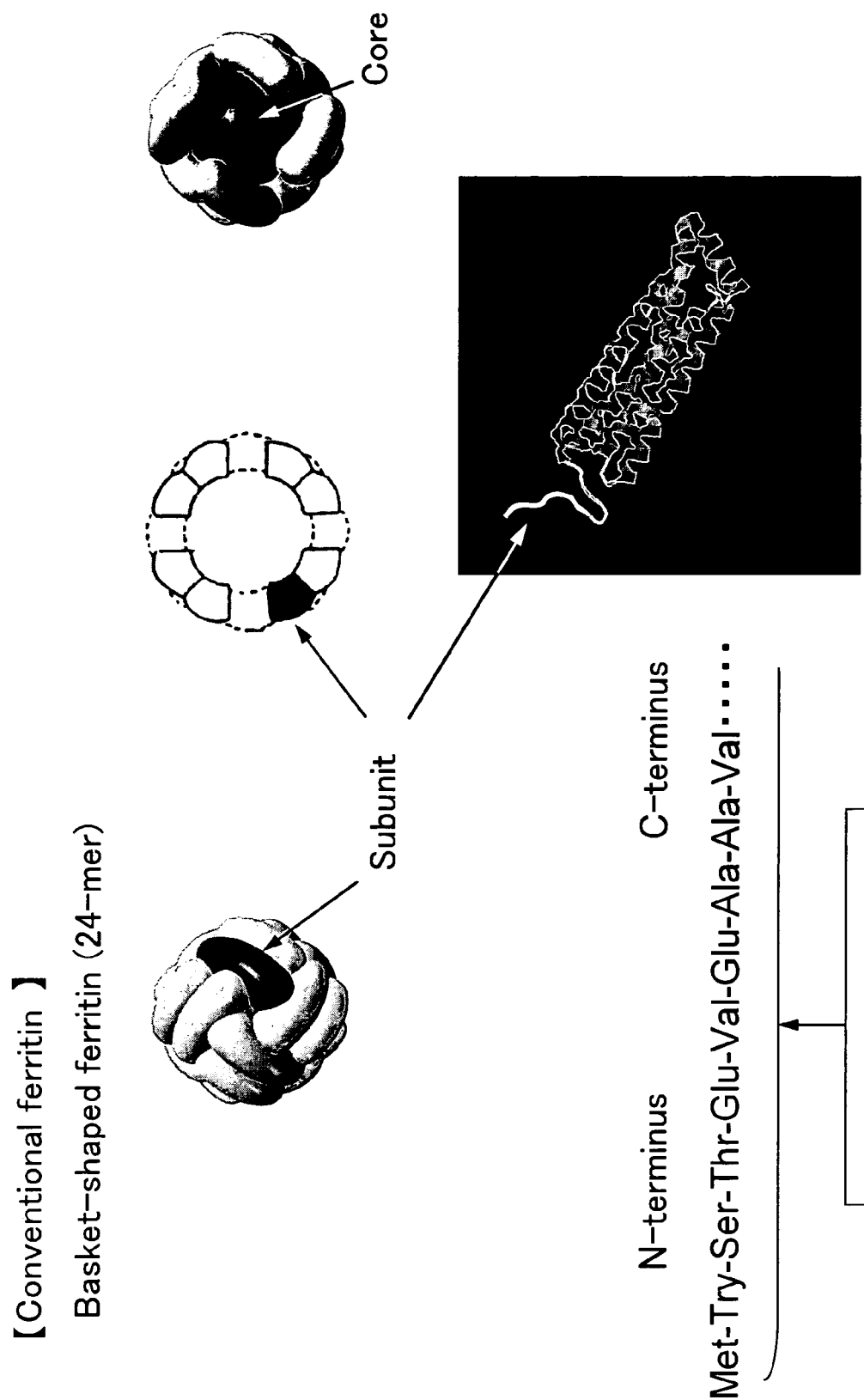
FIG. 4 shows a view illustrating the structure and the like of conventional ferritin.

The structure of conventional ferritin (naturally occurring ferritin (basket-shaped protein)) is illustrated in FIG. 4. Naturally occurring ferritin is a spherical particle having a diameter of about 12 nm and having a cavity (diameter: about 7 nm) inside thereof formed through binding of 24 subunits. Various inorganic material particles (core) can be incorporated in this cavity. One subunit has a specific tertiary structure as shown in the center of FIG. 4, which was analyzed in detail with X-ray analyses and the like revealing that it includes a combination of secondary structures of α-helix and β-sheet.

Amino acid side chains are protruded from the skeleton (folded polypeptide main chain) of this protein in various directions, and the sequence of the amino acid residues allows each protein to have unique chemical characteristics. The ferritin surface reflects the features of the protruded amino acid residues, thereby determining the chemical characteristics of the entire protein (interaction with the base material, interaction among the proteins and the like).

Because there are L type and H type subunits having slightly different structures. Therefore, the naturally occurring ferritin does not have a constant structure. In the following embodiments, recombinant ferritin (RF) constructed with only L type subunits was used.

First, a DNA encoding L type ferritin (SEQ ID NO: 2, 528 base pairs) was amplified with a PCR method to prepare a large amount of L type ferritin DNA. Next, this L type ferritin DNA was cleaved at sites where restriction enzymes EcoRI and Hind III will specifically cleave (restriction enzyme sites). By this cleavage treatment, a solution of L type ferritin DNA fragments having restriction enzyme sites of EcoRI and Hind III was prepared. DNA electrophoresis of this solution was performed, and the DNA fragments encoding the L type ferritin alone were recovered and purified.

Thereafter, this L type ferritin DNA fragment and a vector plasmid (pMK-2) which had been treated with restriction enzymes EcoRI-Hind III were incubated to perfect ligation. Accordingly, a vector plasmid pMK-2-fer-0 having the L type ferritin DNA incorporated at the multicloning site (MSC) of the pMK-2 plasmid was produced. The vector plasmid pMK-2 employed was selected in light of advantages in obtaining a large amount of ferritin because it has Tac promoter as its promoter, and thus is characterized by the large copy number as a multicopy plasmid.

Figure 5:
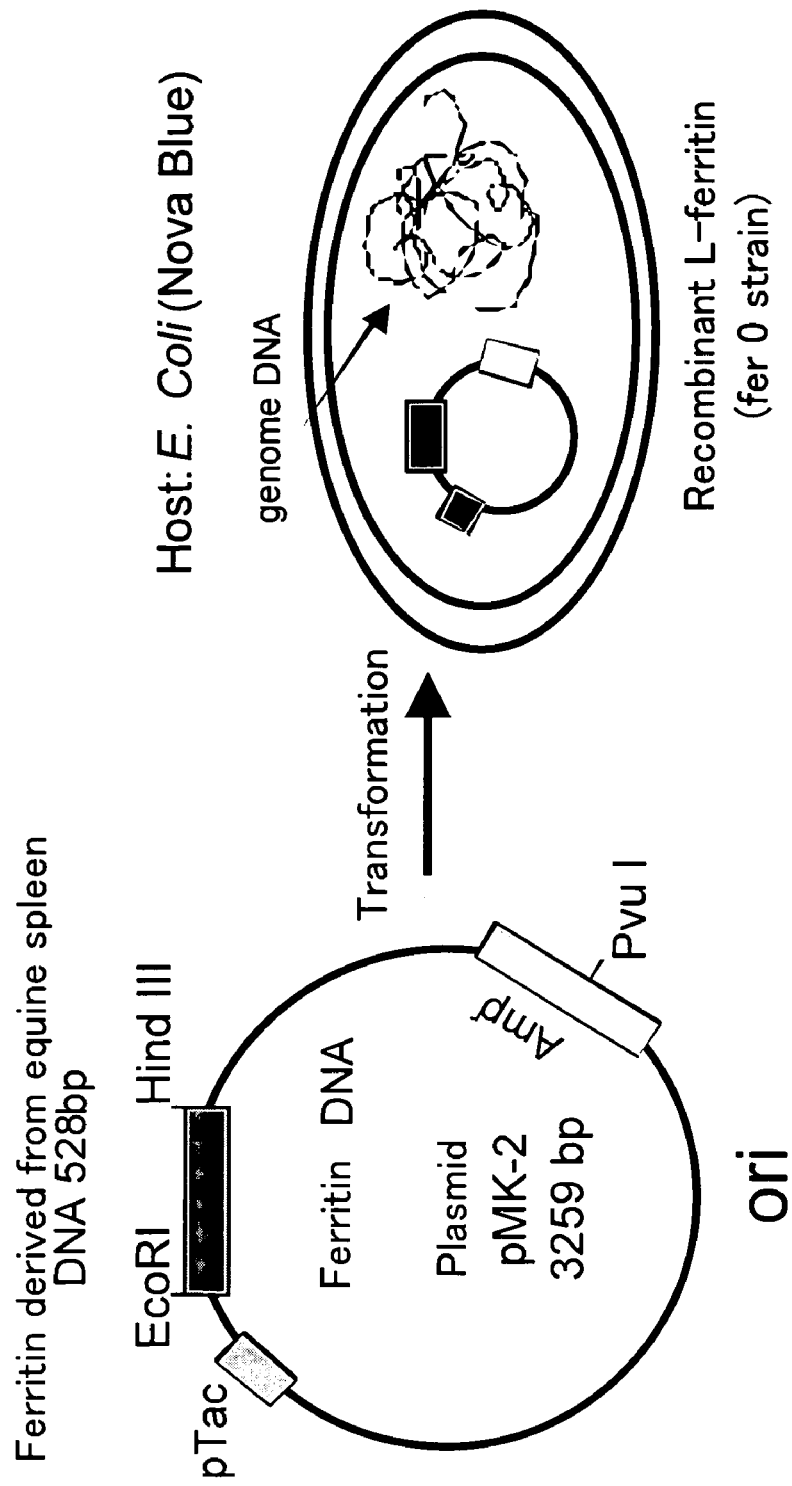
FIG. 5 shows a schematic view illustrating the principal construction of a plasmid of L type ferritin subunit, and incorporation of the plasmid into *Escherichia coli*.

Thus produced plasmid (pMK-2-fer-0) was introduced (transformed) into *E. coli* Nova Blue (Novagen), a strain of *Escherichia coli*, as a host, thereby yielding a recombinant L type ferritin strain (fer-0). Schematic view illustrating the principal construction of the plasmid of the L type ferritin subunit, and incorporation of the plasmid into *Escherichia coli* is shown in FIG. 5.

Inside of the recombinant ferritin was included an inorganic particle required for producing a group of nanoparticles for constituting a floating gate. It was suggested that thermostability of the recombinant ferritin (fer-0) produced according to the aforementioned method is improved by the addition at the amino terminus. Although the naturally occurring ferritin had an allowable temperature limit of approximately 55° C., in contrast, fer-0 had an allowable temperature limit of 95° C. By virtue of this heat resistance, synthesis of nanoparticles utilizing a basket-shaped protein at a high temperature which had been conventionally impossible was enabled.

<Method for Manufacturing Titanium-Binding Ferritin>

Next, a method for manufacturing titanium-binding ferritin (TBF) including modification with a titanium-binding peptide (SEQ ID NO: 1) at the N-terminal part will be explained.

Figure 6:
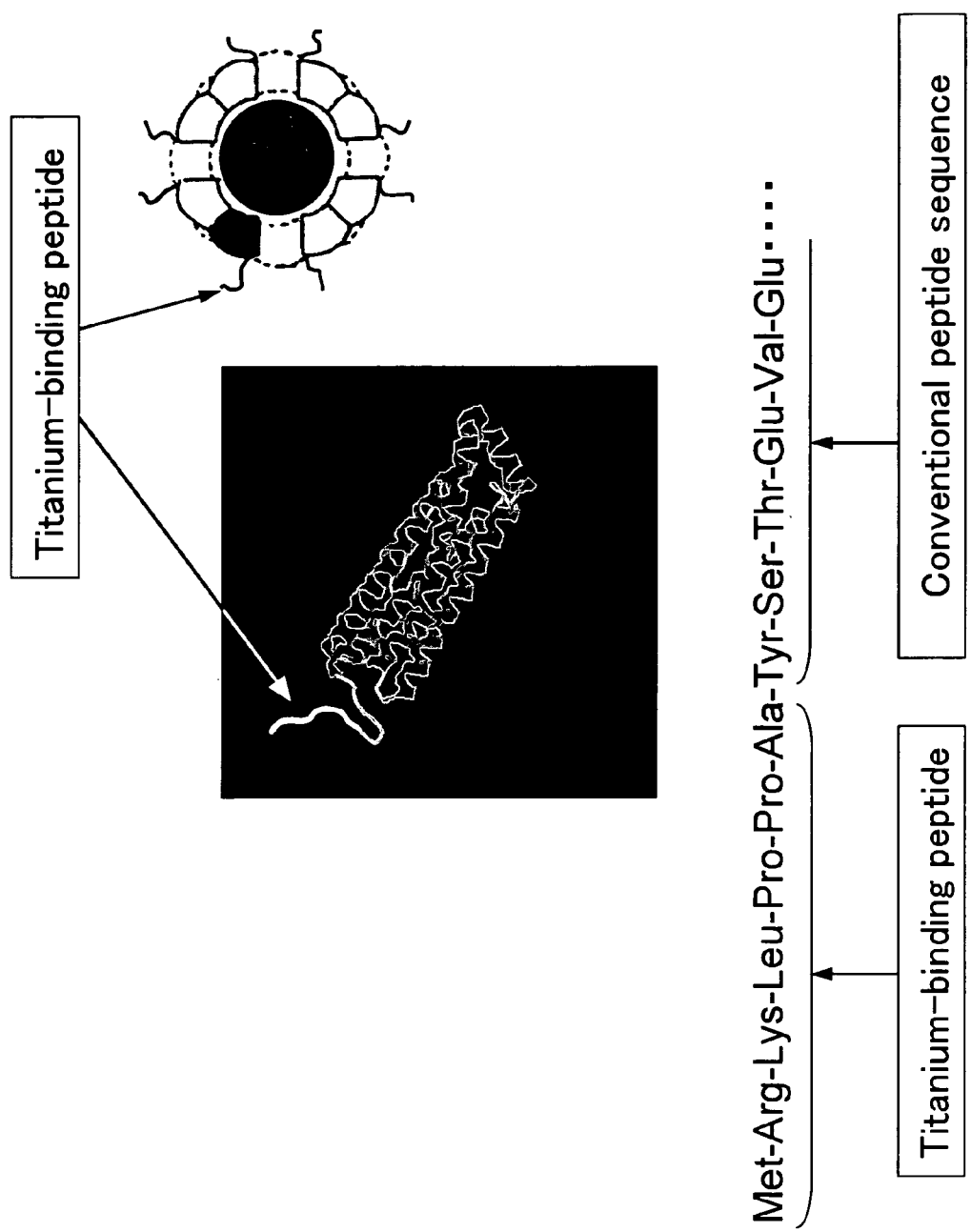
FIG. 6 shows a view illustrating the structure (SEQ ID NO:1) and the like of the titanium-binding ferritin of the present invention.

When the amino terminus (N-terminus) of the subunit constructing ferritin is modified with a peptide, a structure including this peptide protruded outside of the ferritin particle as shown in FIG. 6 is provided. Hence, through modification with an arbitrary peptide (titanium-binding peptide in FIG. 6) at this N-terminal part, modification of the surface of the ferritin fine particle with this peptide is enabled.

Hereinafter, a specific method for manufacturing ferritin (SEQ ID NO: 5) including the peptide having the amino acid sequence set out in SEQ ID NO: 1 added and modified at the N-terminus will be demonstrated. A full length gene of the L type subunit of naturally occurring ferritin (derived from equine liver) is set out in SEQ ID NO: 2. It was reported that 7 residues among amino residues synthesized from N-terminal 24 bases are processed and deleted in nature.

In other words, ferritin having the amino acid sequence set out in SEQ ID NO: 3 should be synthesized from the DNA set out in SEQ ID NO: 2, however, ferritin having the amino acid sequence set out in SEQ ID NO: 4 is yielded in fact because 7 amino acid residues of from the second to the eighth are deleted from the N-terminus.

The present inventor found a method for arrangement in which ferritin including a titanium-binding peptide (SEQ ID NO: 1) added and modified at the N-terminus is synthesized, thereby forming a flexible titanium-binding peptide with variable structure to the outside of the ferritin particle to allow the ferritin modified with this peptide to be selectively adsorbed to titanium.

First, a DNA (SEQ ID NO: 6 (30 base pairs) encoding a titanium-binding peptide (SEQ ID NO: 1) and SEQ ID NO: 7 (22 base pairs)) were amplified with a PCR method to prepare a large amount of DNA.

Next, the DNA and a vector plasmid (pMK-2) encoding human recombinant L type ferritin which had been treated with restriction enzymes Bam I and Sac I were incubated to perfect ligation. Accordingly, a vector plasmid (pKIS1) having the DNA of the aforementioned base sequence and L type ferritin DNA incorporated into the multicloning site (MSC) of the pMK-2 plasmid was produced. The vector plasmid pMK-2 employed for the production of pKIS1 was selected in light of advantages in obtaining a large amount of ferritin because it has Tac promoter as its promoter, and thus is characterized by the large copy number as a multicopy plasmid.

Thus produced plasmid was introduced (transformed) into *E. coli* Nova Blue (Novagen), a strain of *Escherichia coli*, as a host, thereby yielding a titanium-binding L type ferritin strain.

As explained in the foregoings, according to the method for arranging titanium-binding ferritin of the present invention, the steps are extremely simplified because binding force between the titanium-binding ferritin and titanium on the substrate can be controlled by the titanium-binding ferritin per se.

[Method for Arranging Inorganic Particles on the Substrate]

Next, the method for arranging inorganic particles of the present invention will be explained by way of FIGS. 7A and 7B. Herein, an example in which ferric oxide ($Fe_2O_3$) was used as the inorganic particle will be demonstrated.

Figure 7:
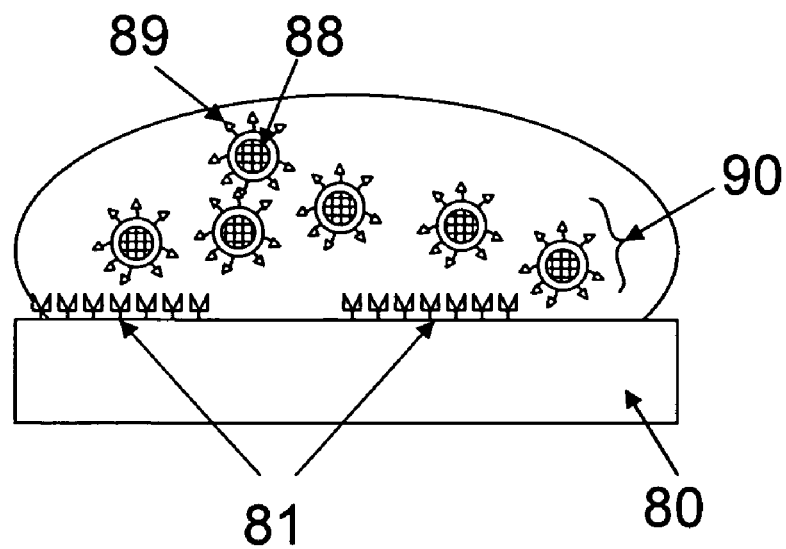
FIGS. 7A and 7B show an explanatory view illustrating the aspect of the method for arranging inorganic particles of the present invention.
Figure 7:

In the step shown in FIG. 7A, after adding dropwise a solution of titanium-binding ferritin 89 including $Fe_2O_3$ 88 (titanium-binding ferritin including $Fe_2O_3$ 90) therein to a substrate 80 having a titanium region 81 where arrangement of ferritin is required, followed by incubation for a given time period, the substrate was washed with pure water.

Figure 7B:
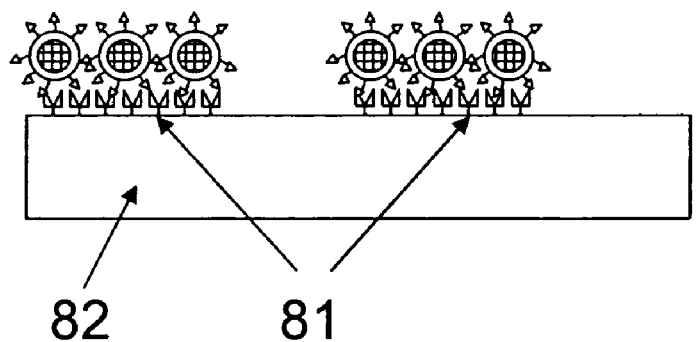

Next, in the step shown in FIG. 7B, because the titanium-binding ferritin 89 is specifically adsorbed in the titanium region 81 on the substrate 80, $Fe_2O_3$ 88 included therein can be also arranged in the titanium region 81. As a consequence, the substrate 82 having ferritin selectively arranged only in the titanium region can be produced.

Figure 8:
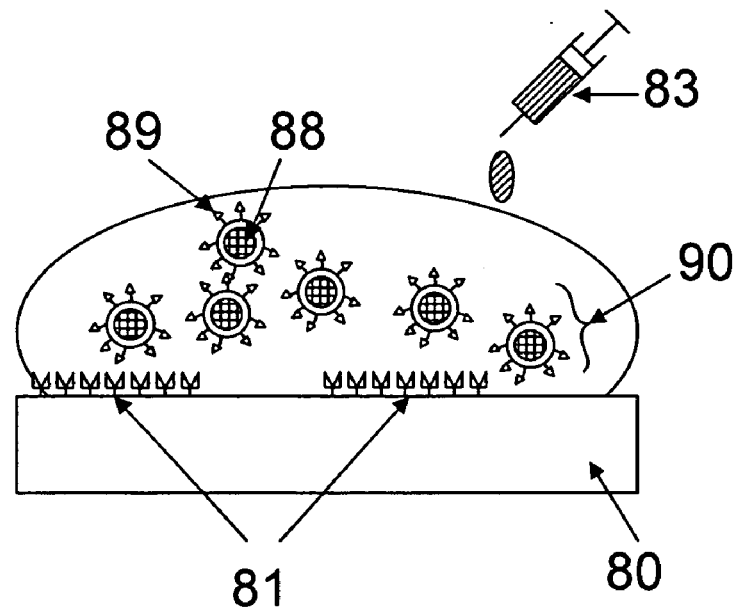
FIGS. 8A and 8B show an explanatory view illustrating the aspect of a modified example of the method for arranging inorganic particles of the present invention.
Figure 8:
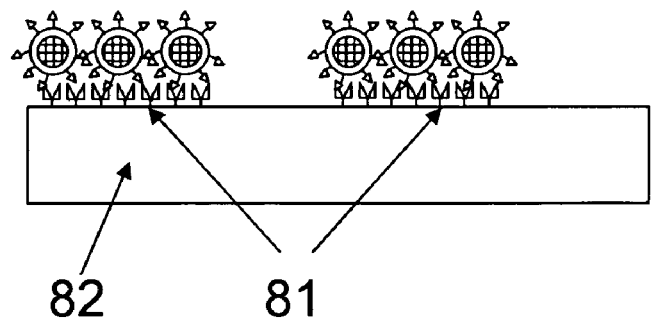

Also, as the alternative example of the method described above, as shown in FIGS. 8A and 8B, a nonionic surface activating agent 83 can be added also to the solution of titanium-binding ferritin 89 including $Fe_2O_3$ 88 therein. Accordingly, further improvement of the selective binding property of the titanium-binding ferritin 89 to titanium is enabled.

In Embodiments described below, TBF which had been including $Fe_2O_3$ therein was baked to burn out by heating at 500° C. in nitrogen gas after washing with water, whereby allowing $Fe_2O_3$ to be fixed in the titanium region 81. In place of the nitrogen gas, an inert gas or oxygen gas, hydrogen gas or the like can be also used. Moreover, also in the case in which conventional recombinant ferritin is used in place of the titanium-binding ferritin, similar process as described above was performed.

Next, introduction of the inorganic particle into titanium-binding ferritin as described above will be explained.

<Introduction of Inorganic Particle into Titanium-Binding Ferritin>

In the present invention, type of the inorganic particle to be included into the recombinant ferritin (RF) is not particularly limited, but in the foregoing descriptions and Embodiments described later, ferric oxide ($Fe_2O_3$) was used as the inorganic particle. Introduction of the $Fe_2O_3$ core into TBF was conducted as described below.

As the reaction solution, 0.5 mg/ml TBF/100 mM HEPES-NaOH (pH 7.0) was prepared, and thereto was added 5 mM ammonium iron acetate. The reaction was allowed at 25° C. overnight, and TBF having the core of $Fe_2O_3$ formed was recovered from the solution following the reaction through molecular purification by centrifugal separation and gel filtration. The centrifugal separation was conducted under the conditions of 1,600 G for 10 min, and 10,000 G for 30 min. Thus, unwanted portions other than TBF were eliminated stepwise as the precipitate, and then TBF having a $Fe_2O_3$ core formed therein was recovered from the finally remaining supernatant by ultracentrifugal separation at 230,000 G for 1 hour as the pellet. Thus resulting TBF was loaded on gel filtration using HPLC [column: TSK-GEL G4000SWXL PEEK/flow rate: 1 ml/min/buffer: 50 mM Tris-HCl (pH 8.0)+ 150 mM NaCl] to fractionate to give a peak of 24-mer (about 480 kDa). Solution of the fractionated TBF was concentrated using an ultrafilter to obtain TBF including $Fe_2O_3$ therein.

In addition, by carrying out a similar operation to that described above on RF, RF including $Fe_2O_3$ therein was obtained.

Hereinafter, specific embodiments of the present invention will be explained sequentially.

Embodiment 1

Embodiment 1 of the present invention demonstrates a method for arranging titanium-binding ferritin and inorganic particles on a substrate. In this Embodiment, a Pt part and a Ti part are formed on the substrate.

Specific examples of this Embodiment will be shown by way of Examples below, and the effect thereof will be explained with reference to Comparative Examples.

EXAMPLE 1

Figure 9B:
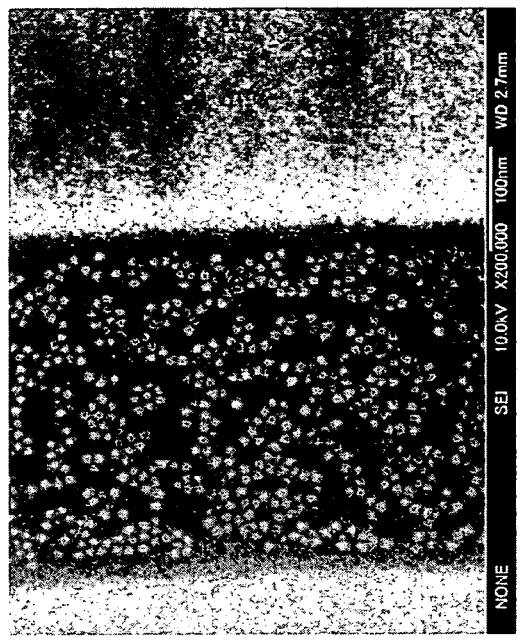
FIG. 9B shows a scanning transmission electron micrograph of the substrate surface according to Example 1.
Figure 9A:
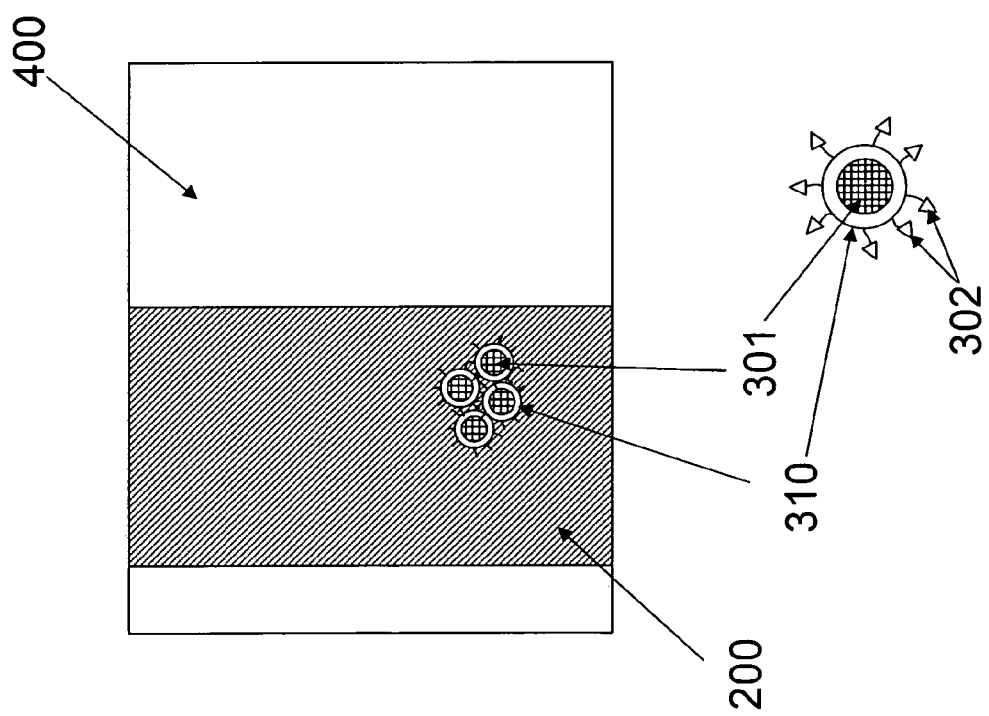
FIG. 9A shows a schematic explanatory view with respect to Example 1.

First, FIG. 9A shows a schematic view illustrating an experiment in which TBF 310 including modification of the surface thereof with a peptide 302 which specifically adsorbs to Ti, and including $Fe_2O_3$ 301 therein was arranged on a Ti substrate 200 with a platinum membrane (Pt) 400 formed in a part of the surface thereof.

In Example 1, the inorganic particles were arranged on the substrate as in the followings.

TBF 310 including $Fe_2O_3$ 301 therein was adjusted to give the concentration of 2 mg/ml with a buffer solution (10 mM Tris-HCl, pH 8.0). On the Ti substrate 200 having a platinum membrane (Pt) formed in a part of the surface was added the TBF solution dropwise. After leaving to stand at room temperature for 1 hour, it was washed with pure water. After washing, the substrate was subjected to a heat treatment according to the method described above, thereby allowing $Fe_2O_3$ 301 to be fixed on the substrate.

FIG. 9B shows a scanning transmission electron micrograph of the substrate surface after allowing the $Fe_2O_3$ 301 to be fixed as corresponded to the schematic view shown in FIG. 9A. $Fe_2O_3$ 301 was selectively arranged on the Ti substrate 200, therefore, it was verified that TBF 310 did not adsorb to the Pt membrane 400 but specifically adsorbed to the Ti substrate 200. Hence, absorptive force between ferritin and the base material on the substrate could be controlled by modification of the ferritin surface with a peptide.

EXAMPLE 2

In Example 2, Tween 20 manufactured by ICI Inc., which is a nonionic surface activating agent was added in an amount of 0.5 v/v % to the buffer solution. As a result of a similar operation to that in Example 1, it was verified that TBF 310 did not adsorb to the Pt membrane 400, but almost all thereof specifically adsorbed to the Ti substrate 200. In other words, addition of Tween 20 improved selective adsorptivity of TBF to the Ti substrate.

Embodiment 2

Embodiment 2 of the present invention demonstrates a method for arranging titanium-binding ferritin and inorganic particles on a substrate. In this Embodiment, a silicon oxide ($SiO_2$) part and a Ti part are formed on the substrate.

EXAMPLE 3

In Example 3, the inorganic particles were arranged on the substrate as in the followings.

TBF including $Fe_2O_3$ therein was adjusted to give the concentration of 2 mg/ml with a buffer solution (10 mM Tris-HCl, pH 8.0). On a silicon oxide ($SiO_2$) substrate 100 having a titanium membrane (Ti) formed in a part of the surface was added the TBF solution dropwise. After leaving to stand at room temperature for 1 hour, it was washed with pure water. After washing, the substrate was subjected to a heat treatment according to the method described above, thereby allowing $Fe_2O_3$ to be fixed on the substrate.

When the scanning transmission electron micrograph of the substrate surface following the fixation of $Fe_2O_3$ was ascertained, $Fe_2O_3$ was hardly arranged on the $SiO_2$ substrate, but was selectively arranged on the Ti membrane. Therefore, it was verified that TBF 310 did not adsorb to the $SiO_2$ substrate 100, but specifically adsorbed to the Ti membrane 200.

EXAMPLE 4

In Example 4, Tween 20 manufactured by ICI Inc., which is a nonionic surface activating agent was added in an amount of 0.5 v/v % to the buffer solution. As a result of a similar operation to that in Example 3, it was verified that TBF 310 did not adsorb to the $SiO_2$ substrate 100, but almost all part thereof specifically adsorbed to the Ti membrane 200. In other words, addition of Tween 20 improved selective adsorptivity of TBF to the Ti membrane.

Embodiment 3

Embodiment 3 of the present invention demonstrates a method for arranging titanium-binding ferritin and inorganic particles on a substrate, the method including addition of a nonionic surface activating agent.

Evaluation of Synergistic Effect with Nonionic Surface Activating Agent, and Selective Arrangement Ratio

COMPARATIVE EXAMPLE 1

In Comparative Example 1, inorganic particles were arranged on a substrate as described below.

Figures 10A, 10B:
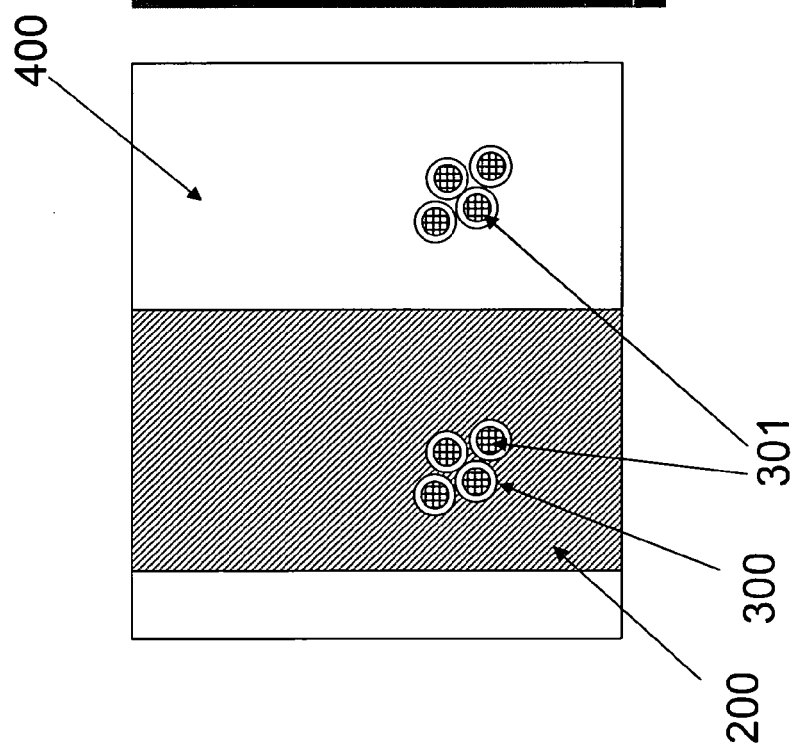
FIG. 10A shows a schematic explanatory view with respect to Comparative Example 1.
FIG. 10B shows a scanning transmission electron micrograph of the substrate surface according to Comparative Example 1.

FIG. 10A shows a schematic view illustrating an experiment in which naturally occurring ferritin (NF) 300 derived from equine spleen including $Fe_2O_3$ 301 therein was arranged on a Ti substrate 200 with a platinum membrane (Pt) 400 in a part of the surface. The experiment was carried out under the conditions that are completely the same as those in Example 1 except that NF was used in place of TBF. In this step, any nonionic surface activating agent was not used.

FIG. 10B shows a scanning transmission electron micrograph of the substrate after subjecting to the heat treatment as corresponded to FIG. 10A. $Fe_2O_3$ was arranged on both the Pt membrane and the Ti substrate, suggesting no selectivity at all for the base material. The number of $Fe_2O_3$ arranged on the Ti substrate and the Pt membrane was 79 and 76, respectively, exhibiting the selective arrangement ratio of 1.0.

Herein, the selective arrangement ratio means the ratio of the number $N_{(Ti)}$ of $Fe_2O_3$ adsorbed on the Ti to the number $N_{(Pt)}$ of $Fe_2O_3$ adsorbed on the Pt, i.e., $N_{(Ti)}/N_{(Pt)}$. Moreover, with respect to the number of adsorption of $Fe_2O_3$, the number of $Fe_2O_3$ within a region of a square of 200 nm was counted in the scanning transmission electron micrograph of the substrate surface.

COMPARATIVE EXAMPLE 2

In Comparative Example 2, the inorganic particles were arranged on the substrate as in the followings.

When Tween 20 manufactured by ICI Inc., in an amount of 0.5 v/v % was added as a nonionic surface activating agent to the buffer solution of NF including $Fe_2O_3$ therein, the number of $Fe_2O_3$ arranged on the Pt membrane was 12, but in contrast, the number of $Fe_2O_3$ arranged on the Ti substrate was 79, exhibiting the selective arrangement ratio of 6.6. Also in the case in which 0.5 v/v % Tween 80 manufactured by ICI Inc., was added as the nonionic surface active agent, completely the same results were achieved.

COMPARATIVE EXAMPLE 3

In Comparative Example 3, the inorganic particles were arranged on the substrate as in the followings.

When the buffer solution of NF including $Fe_2O_3$ therein was added dropwise after adding a solution containing 0.5 v/v % Tween 20 or Tween 80 dropwise to the substrate, the number of $Fe_2O_3$ arranged on the Pt membrane was 13, but in contrast, the number of $Fe_2O_3$ arranged on the Ti substrate was 77, exhibiting the selective arrangement ratio of 6.6. Also in the case in which the buffer solution of RF including $Fe_2O_3$ therein was added dropwise after adding a solution containing 0.5 v/v % Tween 20 or Tween 80 dropwise to the substrate, completely the same results were achieved.

EXAMPLE 5

A similar operation to that in Example 1 was carried out except that a solution containing TBF was added dropwise after adding a solution containing 0.5 v/v % Tween 20 manufactured by ICI Inc., in the buffer solution as the nonionic surface activating agent dropwise onto the substrate.

Experimental results on the Examples and Comparative Examples described above are shown in Table 1.

TABLE 1

| Method of arrangement | Naturally occurring ferritin | | Titanium-binding ferritin | |
|---|---|---|---|---|
| 1. No treatment of ferritin solution, substrate with surface activating agent | On Ti: 79<br>On Pt: 76 | Selective arrangement ratio: 1.0 [Comparative Example 1] | On Ti: 250<br>On Pt: 30 | Selective arrangement ratio: 8.3 [Example 1] |
| 2. 0.5 v/v % nonionic surface activating agent added to ferritin solution | On Ti: 79<br>On Pt: 12 | Selective arrangement ratio: 6.6 [Comparative Example 2] | On Ti: 200<br>On Pt: 1 | Selective arrangement ratio: 200.0 [Example 2] |
| 3. Solution containing 0.5 v/v % nonionic surface activating agent added dropwise to the substrate, followed by addition of ferritin solution dropwise | On Ti: 77<br>On Pt: 13 | Selective arrangement ratio: 6.6 [Comparative Example 3] | On Ti: 200<br>On Pt: 1 | Selective arrangement ratio: 200.0 [Example 5] |

Experimental results of Example 1 revealed that $Fe_2O_3$ arranged on the Pt membrane was 30, but in contrast, $Fe_2O_3$ arranged on the Ti substrate was 250, exhibiting the selective arrangement ratio of 8.3. Meanwhile, in Example 2, $Fe_2O_3$ arranged on the Pt membrane was 1, but in contrast, $Fe_2O_3$ arranged on the Ti substrate was 200, exhibiting the selective arrangement ratio of 200, which was increased about 24 times the ratio in Example 1. Also in the case in which 0.5 v/v % Tween 80 manufactured by ICI Inc., was added as the nonionic surface active agent, completely similar results were achieved.

the Ti substrate surface. In particular, by using a nonionic surface activating agent in combination with TBF, the selectivity could be dramatically improved.

Tween 20 and Tween 80 used herein as the nonionic surface active agent are substances characterized by: belonging to polyoxyethylene sorbitans (polyoxyethylene sorbitan alkyl esters), being readily dissolved particularly at a low temperature, not having a group dissociable into an ion in the aqueous solution, and the hydrophilicity thereof being adjustable. General structural formulae of Tween 20 and Tween 80 are shown below.

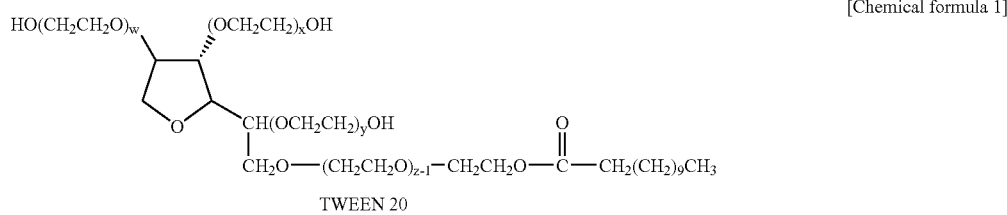

[Chemical formula 1]

TWEEN 20

Sum of w + x + y + z = 20

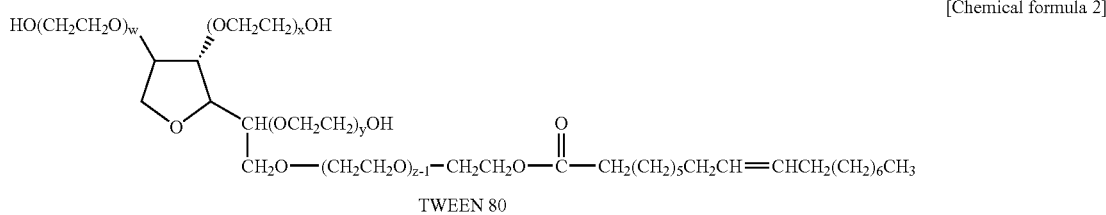

[Chemical formula 2]

TWEEN 80

Sum of w + x + y + z = 20

Moreover, when a solution containing 0.5 v/v % Tween 20 or Tween 80 was added dropwise to the substrate in Example 5, followed by adding a buffer solution of TBF including $Fe_2O_3$ therein dropwise, completely similar results to those in Example 2 were achieved.

Hence, modification of the surface of ferritin, which inherently has no selective adsorptivity for Ti substrates and Pt membranes at all, with a peptide that specifically binds to Ti enabled specific enhancement of adsorptivity to the Ti substrate surface, thereby allowing for specific arrangement on When the concentration of the added nonionic surface activating agent is less than 0.006 v/v %, adsorption controllability for RF and TBF was decreased, the selective arrangement ratio was lowered. In contrast, when the concentration of the nonionic surface activating agent was beyond 10 v/v %, the amount of adsorption to the Ti membrane was decreased. Therefore, in light of the practicability, the nonionic surface activating agent in the solution containing ferritin according to the present invention preferably falls within the range of concentration of 0.006 v/v % or greater and 10 v/v % or less, and more preferably falls within the range of concentration of 0.01 v/v % or greater and 1 v/v % or less.

Embodiment 4

Embodiment 4 of the present invention demonstrates a method for reverse-selective arrangement of titanium-binding ferritin and inorganic particles on a substrate.

Method for Reverse-Selective Arrangement of Inorganic Particles Using Apoferritin In Embodiments 1 and 2, the method for arranging ferritin and inorganic particles in the region where ferritin is specifically adsorbed was explained. A method for arranging protein and inorganic particles in a region other than the region where ferritin is specifically adsorbed in a reverse manner will be explained with reference to FIGS. 11A to 11E.

Figure 11A:
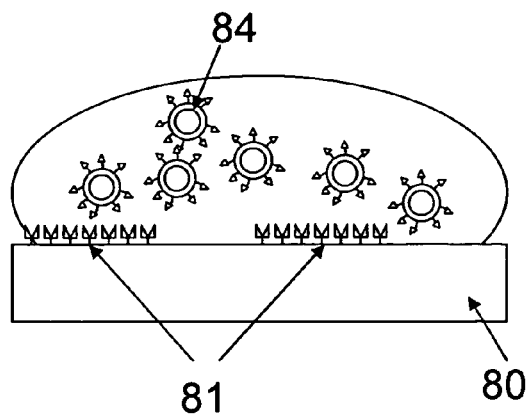
FIGS. 11A to 11E show an explanatory view illustrating the method for reverse-selectively arranging inorganic particles according to Embodiment 4 of the present invention.

First, in the step shown in FIG. 11A, a solution containing TBF (apoferritin) 84 without including $Fe_2O_3$ therein is added dropwise to a substrate 80 having a titanium region 81 in a part of the surface. Then, after incubation for a predetermined time period, the substrate is washed with pure water.

Figure 11B:
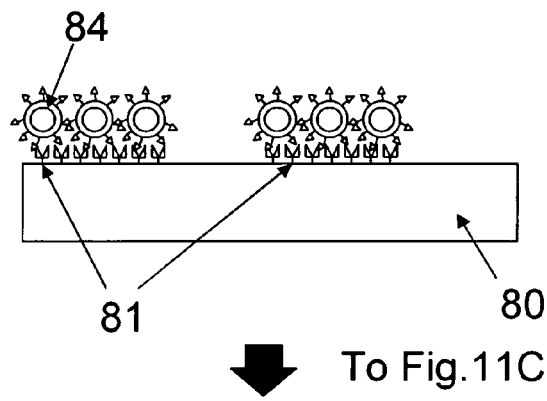

Next, in the step shown in FIG. 11B, TBF 84 adsorbs only in the titanium region 81, thereby giving the substrate 80 with selective arrangement.

Figure 11C:
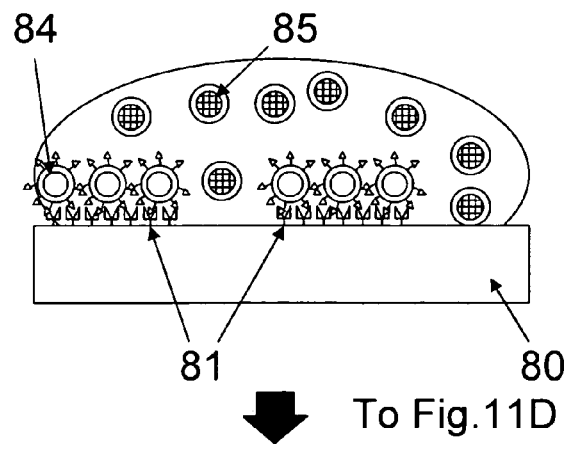

Next, in the step shown in FIG. 11C, a solution containing RF 85 including an inorganic particle therein is added dropwise to the substrate 80, and a similar operation to that described above is carried out. In this step, any nonionic surface active agent is not used.

Figure 11D:
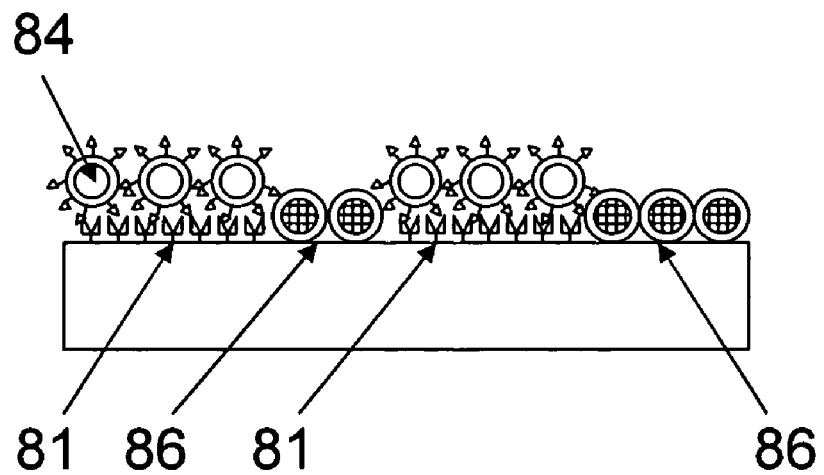
Figure 11D:

Next, in the step shown in FIG. 11D, RF 85 including an inorganic particle therein is adsorbed only in a region 86 where arrangement of the inorganic particles is required which is a region other than the titanium region 81 where TBF 84 was already adsorbed.

Figure 11E:
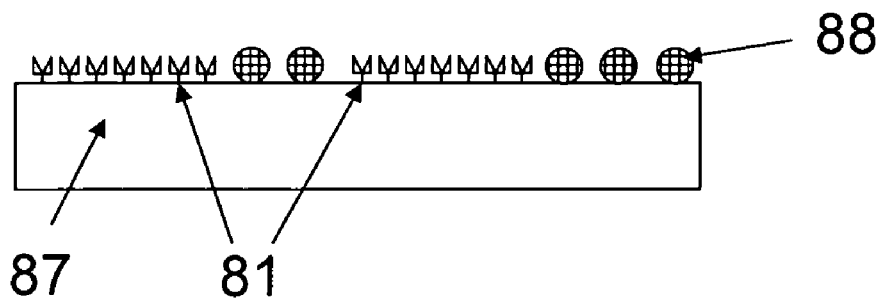

Thereafter, in the step shown in FIG. 11E, the substrate 80 is heated according to the method described above, whereby obtaining a substrate 87 having inorganic particle 88 reverse-selectively arranged in the region other than the titanium region 81.

The protein including an inorganic particle therein is not limited to RF but other type of protein can be used. Also, in place of RF including an inorganic particle therein, a protein without including an inorganic particle therein can be also reverse-selectively arranged. This technique shall be useful in the cases in which, for example, an enzyme having a certain function is arranged in a specified region on a substrate to manufacture a biosensor.

In addition, $Fe_2O_3$ was selectively arranged on a titanium membrane on a substrate using ferritin including $Fe_2O_3$ therein as an inorganic particle in the above Embodiments, however, just the same results shall be achieved when ferritin without including any inorganic particle therein is used.

From the foregoing description, many modifications and other embodiments of the present invention will be apparent to persons skilled in the art. Therefore, the foregoing description should be construed as merely illustrative exemplification, which was provided for the purpose of teaching the best embodiment for carrying out the present invention to persons skilled in the art. Details of the constitution and/or function of the present invention can be substantially altered without departing from the spirit thereof.

The present invention relates to a method for selectively arranging ferritin or inorganic particles on a substrate with high mass productivity and favorable cost performances. In particular, a technique for selectively arranging inorganic particles having a diameter of several to several ten nanometers in a region where required, or for regularly arranging them in a nano-region is provided. According to this technique, arrangement of inorganic material particles on a required base material on a substrate in a self-selective manner on a nano-scale level is enabled. The technique can be applied in manufacture steps in industrial fields of catalysts, sensors, biochips, transistors, semiconductor lasers, magnetic discs, displays and the like.

What is claimed is:

1. A method for arranging ferritin, said method comprising a binding step in which a solution containing a titanium-binding ferritin including modification at the subunit N-terminal part with a peptide set out in SEQ ID NO: 1 which recognizes and binds to titanium is added dropwise to a substrate with titanium formed on the part of the surface thereof, thereby allowing the titanium-binding ferritin to be selectively bound to titanium.

2. The method for arranging ferritin according to claim 1 wherein said solution further contains a nonionic surface activating agent, and said method comprises following said binding step a removing step in which the nonionic surface activating agent is removed from on said substrate.

3. The method for arranging ferritin according to claim 1 wherein said method comprises prior to said binding step a covering step in which said substrate is covered with a nonionic surface activating agent.

4. The method for arranging ferritin according to claim 2 wherein the concentration of said nonionic surface activating agent is 0.006 v/v % or greater and 10 v/v % or less.

5. The method for arranging ferritin according to claim 1 wherein said titanium-binding ferritin includes an inorganic particle therein.

6. The method for arranging ferritin according to claim 1 wherein said method comprises following said binding step, an arrangement step in which a solution containing ferritin other than the titanium-binding ferritin is added dropwise to said substrate, thereby arranging ferritin other than said titanium-binding ferritin, in a part other than said titanium on said substrate.

7. A method for arranging inorganic particles, said method comprising a binding step in which a solution containing a titanium-binding ferritin including said inorganic particle therein and including modification at the subunit N-terminal part with a peptide set out in SEQ ID NO: 1 which recognizes and binds to titanium is added dropwise onto a substrate with titanium formed on the part of the surface thereof, thereby allowing said titanium-binding ferritin to be selectively bound to titanium on said substrate, and a decomposition step in which said substrate is heated to decompose said titanium-binding ferritin.

8. The method for arranging inorganic particles according to claim 7 wherein said solution further contains a nonionic surface activating agent, and said method comprises between said binding step and said arrangement step a removing step in which the nonionic surface activating agent is removed from on said substrate.

9. The method for arranging inorganic particles according to claim 7 wherein said method comprises prior to said binding step a covering step in which said substrate is covered with a nonionic surface activating agent.

10. The method for arranging inorganic particles according to claim 7 wherein the concentration of said nonionic surface activating agent is 0.006 v/v % or greater and 10 v/v % or less.

11. A method for arranging inorganic particles on a substrate, said method comprising:

a first step in which a solution comprising a titanium-binding ferritin is exposed to a portion of a substrate consisting of titanium, thereby allowing said titanium-binding ferritin to be selectively bound to titanium on said portion of the substrate, said titanium-binding ferritin having a seven N-terminal amino acid sequence as set forth in SEQ ID NO: 1, configured to bind to said portion of the substrate consisting of titanium, a second step in which a solution comprising ferritin containing an inorganic particle, is exposed to the substrate, and a third step in which said substrate is heated to decompose said titanium-binding ferritin and said ferritin containing an inorganic particle on said substrate thereby selectively attaching and arranging the inorganic particles on said substrate.

12. The method for arranging inorganic particles according to claim 11, wherein:

said solution containing a titanium-binding ferritin further contains a nonionic surface activating agent, said method further comprises a removing step after said first step and before said second step, and the nonionic surface activating agent is removed from on said substrate.

13. The method for a arranging inorganic particles according to claim 11, wherein said method comprises prior to said first step, a covering step in which said substrate is covered with a nonionic surface activating agent.

14. The method for arranging inorganic particles according to claim 13, wherein the concentration of said nonionic surface activating agent is between 0.006 v/v % and 10 v/v %.

15. The method for arranging inorganic particles according to claim 11, wherein said inorganic particles comprise ferric oxide.

* * * * *

UNITED STATES PATENT AND TRADEMARK OFFICE
CERTIFICATE OF CORRECTION

PATENT NO. : 7,439,334 B2
APPLICATION NO. : 11/354864
DATED : October 21, 2008
INVENTOR(S) : Ichiro Yamashita et al.

It is certified that error appears in the above-identified patent and that said Letters Patent is hereby corrected as shown below:

IN THE CLAIMS:
        In Column 21, Lines 13 and 14 (Claim 1), change "ferritin including modification at the subunit N-terminal part with a peptide set out in SEQ ID NO: 1 which" to --ferritin having a seven N-terminal amino acid sequence as set forth in SEQ ID NO: 1, which--;
        Line 15 (Claim 1), change "titanium is" to --titanium, is--;
        Line 16 (Claim 1), change "formed on the part" to --formed on a part--;

Line 19 (Claim 2), change "claim 1" to "claim 1,";
        Line 22 (Claim 2), change "binding step a" to --binding step, a--;
        Line 23 (Claim 2), change "from on said" to --from said--;

Line 24 (Claim 3), change "claim 1" to --claim 1,--;
        Line 25 (Claim 3), change "binding step a" to --binding step, a--;

Line 28 (Claim 4), change "claim 2" to --claim 2,--;
        Line 30 (Claim 4), change "agent is 0.006 v/v% or greater and 10 v/v% or less" to --agent is between 0.006 v/v% and 10 v/v%--;

Line 31 (Claim 5), change "claim 1" to --claim 1,--;

In Column 21, Line 35 (Claim 6), change "claim 1" to --claim 1,--;
        Lines 38-41 (Claim 6), change "other than the titanium-binding ferritin is added dropwise to said substrate, thereby arranging ferritin other than said titanium-binding ferritin, in a part other than said titanium on said substrate." to --containing an inorganic particle is added dropwise to said substrate, thereby arranging said ferritin containing an organic particle in part of the substrate other than said titanium bound by said titanium-binding ferritin.--;

Lines 46 and 47 (Claim 7), change "and including modification at the subunit N-terminal part with a peptide set out in SEQ ID NO: 1 which" to --and having a seven N-terminal amino acid sequence as set forth in SEQ ID NO: 1, which--;
        Line 48 (Claim 7), change "to titanium is" to --to titanium, is--;
        Line 54 (Claim 7), change "titanium-binding ferritin." to --titanium-binding ferritin, and thereby selectively attaching and arranging the inorganic particles on said substrate.--;

UNITED STATES PATENT AND TRADEMARK OFFICE
CERTIFICATE OF CORRECTION

PATENT NO.      : 7,439,334 B2
APPLICATION NO. : 11/354864
DATED           : October 21, 2008
INVENTOR(S)     : Ichiro Yamashita et al.

It is certified that error appears in the above-identified patent and that said Letters Patent is hereby corrected as shown below:

Line 56 (Claim 8), change "claim 7 wherein" to --claim 7 wherein,--;
In Column 22, Line 11 (Claim 8), change "step a" to --step, a--;
Line 12 (Claim 8), change "from on said" to --from said--;

In Column 22, Line 15 (Claim 9), change "claim 7 wherein" to --claim 7, wherein--;
Line 16 (Claim 9), change "step a covering" to --step, a covering--;

Line 19 (Claim 10), change "claim 7 wherein" to --claim 7, wherein--;
Line 20 (Claim 10), change "agent is 0.006 v/v % or greater and 10 v/v % or less." to --agent is between 0.006 v/v% and 10 v/v%.--;

Lines 29-31 (Claim 11), change "SEQ ID NO:1, configured to bind to said portion of the substrate consisting of titanium," to --SEQ ID NO: 1, which recognizes and binds to titanium on said portion of the substrate,--;
Line 37 (Claim 11), change "substrate thereby" to --substrate, thereby--; and Line 46 (Claim 12), change "removed from on" to --removed from--.

Signed and Sealed this

Twenty-fourth Day of March, 2009

JOHN DOLL
*Acting Director of the United States Patent and Trademark Office*

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial
<220> FEATURE:
<223> OTHER INFORMATION: Chemically Synthesized

<400> SEQUENCE: 1

Met Arg Lys Leu Pro Pro Ala
1               5

<210> SEQ ID NO 2
<211> LENGTH: 528
<212> TYPE: DNA
<213> ORGANISM: Equus caballus

<400> SEQUENCE: 2
atgagctccc agattcgtca gaattattct actgaagtgg aggccgccgt caaccgcctg      60
gtcaacctgt acctgcgggc ctcctacacc tacctctctc tgggcttcta tttcgaccgc     120
gacgatgtgg ctctggaggg cgtatgccac ttcttccgcg agttggcgga ggagaagcgc     180
```

-continued

```
gagggtgccg agcgtctctt gaagatgcaa accagcgcg gcggccgcgc tctcttccag    240
gacttgcaga agccgtccca ggatgaatgg ggtacaaccc cagacgccat gaaagccgcc    300
attgtcctgg agaagagcct gaaccaggcc cttttggatc tgcatgccct gggttctgcc    360
caggcagacc cccatctctg tagcttcttg tctagccact tcctagacga ggaggtgaaa    420
ctcatcaaga agatgggcga ccatctgacc aacatccaga ggctcgttgg ctcccaagct    480
gggctgggcg agtatctctt tgaaaggctc actctcaagc acgactaa                 528
```

<210> SEQ ID NO 3
<211> LENGTH: 175
<212> TYPE: PRT
<213> ORGANISM: Artificial
<220> FEATURE:
<223> OTHER INFORMATION: Chemically Synthesized

<400> SEQUENCE: 3

Met Ser Ser Gln Ile Arg Gln Asn Tyr Ser Thr Glu Val Glu Ala Ala
1               5                   10                  15

Val Asn Arg Leu Val Asn Leu Tyr Leu Arg Ala Ser Tyr Thr Tyr Leu
            20                  25                  30

Ser Leu Gly Phe Tyr Phe Asp Arg Asp Asp Val Ala Leu Glu Gly Val
        35                  40                  45

Cys His Phe Phe Arg Glu Leu Ala Glu Glu Lys Arg Glu Gly Ala Glu
    50                  55                  60

Arg Leu Leu Lys Met Gln Asn Gln Arg Gly Gly Arg Ala Leu Phe Gln
65                  70                  75                  80

Asp Leu Gln Lys Pro Ser Gln Asp Glu Trp Gly Thr Thr Pro Asp Ala
                85                  90                  95

Met Lys Ala Ala Ile Val Leu Glu Lys Ser Leu Asn Gln Ala Leu Leu
            100                 105                 110

Asp Leu His Ala Leu Gly Ser Ala Gln Ala Asp Pro His Leu Cys Ser
        115                 120                 125

Phe Leu Ser Ser His Phe Leu Asp Glu Glu Val Lys Leu Ile Lys Lys
    130                 135                 140

Met Gly Asp His Leu Thr Asn Ile Gln Arg Leu Val Gly Ser Gln Ala
145                 150                 155                 160

Gly Leu Gly Glu Tyr Leu Phe Glu Arg Leu Thr Leu Lys His Asp
                165                 170                 175

<210> SEQ ID NO 4
<211> LENGTH: 168
<212> TYPE: PRT
<213> ORGANISM: Equus caballus

<400> SEQUENCE: 4

Met Tyr Ser Thr Glu Val Glu Ala Ala Val Asn Arg Leu Val Asn Leu
1               5                   10                  15

Tyr Leu Arg Ala Ser Tyr Thr Tyr Leu Ser Leu Gly Phe Tyr Phe Asp
            20                  25                  30

Arg Asp Asp Val Ala Leu Glu Gly Val Cys His Phe Phe Arg Glu Leu
        35                  40                  45

Ala Glu Glu Lys Arg Glu Gly Ala Glu Arg Leu Leu Lys Met Gln Asn
    50                  55                  60

Gln Arg Gly Gly Arg Ala Leu Phe Gln Asp Leu Gln Lys Pro Ser Gln
65                  70                  75                  80

-continued

```
Asp Glu Trp Gly Thr Thr Pro Asp Ala Met Lys Ala Ala Ile Val Leu
                85                  90                  95

Glu Lys Ser Leu Asn Gln Ala Leu Leu Asp Leu His Ala Leu Gly Ser
            100                 105                 110

Ala Gln Ala Asp Pro His Leu Cys Ser Phe Leu Ser Ser His Phe Leu
        115                 120                 125

Asp Glu Glu Val Lys Leu Ile Lys Lys Met Gly Asp His Leu Thr Asn
    130                 135                 140

Ile Gln Arg Leu Val Gly Ser Gln Ala Gly Leu Gly Glu Tyr Leu Phe
145                 150                 155                 160

Glu Arg Leu Thr Leu Lys His Asp
                165
```

<210> SEQ ID NO 5
<211> LENGTH: 174
<212> TYPE: PRT
<213> ORGANISM: Artificial
<220> FEATURE:
<223> OTHER INFORMATION: Chemically Synthesized

<400> SEQUENCE: 5

```
Met Arg Lys Leu Pro Ala Tyr Ser Thr Glu Val Glu Ala Ala Val
1               5                   10                  15

Asn Arg Leu Val Asn Leu Tyr Leu Arg Ala Ser Tyr Thr Tyr Leu Ser
            20                  25                  30

Leu Gly Phe Tyr Phe Asp Arg Asp Asp Val Ala Leu Glu Gly Val Cys
        35                  40                  45

His Phe Phe Arg Glu Leu Ala Glu Glu Lys Arg Glu Gly Ala Glu Arg
    50                  55                  60

Leu Leu Lys Met Gln Asn Gln Arg Gly Gly Arg Ala Leu Phe Gln Asp
65                  70                  75                  80

Leu Gln Lys Pro Ser Gln Asp Glu Trp Gly Thr Thr Pro Asp Ala Met
                85                  90                  95

Lys Ala Ala Ile Val Leu Glu Lys Ser Leu Asn Gln Ala Leu Leu Asp
            100                 105                 110

Leu His Ala Leu Gly Ser Ala Gln Ala Asp Pro His Leu Cys Ser Phe
        115                 120                 125

Leu Ser Ser His Phe Leu Asp Glu Glu Val Lys Leu Ile Lys Lys Met
    130                 135                 140

Gly Asp His Leu Thr Asn Ile Gln Arg Leu Val Gly Ser Gln Ala Gly
145                 150                 155                 160

Leu Gly Glu Tyr Leu Phe Glu Arg Leu Thr Leu Lys His Asp
                165                 170
```

<210> SEQ ID NO 6
<211> LENGTH: 30
<212> TYPE: DNA
<213> ORGANISM: Artificial
<220> FEATURE:
<223> OTHER INFORMATION: Chemically Synthesized

<400> SEQUENCE: 6
gatccatgcg caaacttccg gatgcgagct                                     30

<210> SEQ ID NO 7
<211> LENGTH: 22
<212> TYPE: DNA
<213> ORGANISM: Artificial
<220> FEATURE:

-continued

```
<223> OTHER INFORMATION: Chemically Synthesized

<400> SEQUENCE: 7
cgcatccgga agtttgcgca tg                                                    22
```